United States Patent [19]

Whitfield et al.

[11] Patent Number: 5,879,365
[45] Date of Patent: Mar. 9, 1999

[54] SURGICAL CUTTING APPARATUS

[75] Inventors: Kenneth H. Whitfield, New Haven; George Chelednik, Bethel; David L. Cortez, Brookfield, all of Conn.

[73] Assignee: United States Surgical Corporation, Norwalk, Conn.

[21] Appl. No.: 542,762

[22] Filed: Oct. 13, 1995

Related U.S. Application Data

[63] Continuation-in-part of Ser. No. 416,268, Apr. 4, 1995, abandoned.

[51] Int. Cl.$^6$ ..................................................... A61B 17/32
[52] U.S. Cl. ............................................................. 606/180
[58] Field of Search .............................. 606/83, 170, 171, 606/180; 128/751, 753, 754; 604/22

[56] References Cited

U.S. PATENT DOCUMENTS

| | | |
|---|---|---|
| Re. 33,258 | 7/1990 | Onik et al. . |
| 3,606,878 | 9/1971 | Kellogg, Jr. . |
| 4,099,529 | 7/1978 | Peyman . |
| 4,111,207 | 9/1978 | Seiler, Jr. . |
| 4,201,213 | 5/1980 | Townsend . |
| 4,246,902 | 1/1981 | Martinez . |
| 4,282,884 | 8/1981 | Boebel . |
| 4,336,238 | 6/1982 | Holmes et al. . |
| 4,369,788 | 1/1983 | Goald . |
| 4,461,305 | 7/1984 | Cibley . |
| 4,530,356 | 7/1985 | Helfgott et al. . |
| 4,589,414 | 5/1986 | Yoshida et al. . |
| 4,603,694 | 8/1986 | Wheeler . |
| 4,620,547 | 11/1986 | Boebel ...................................... 128/754 |
| 4,651,753 | 3/1987 | Lifton ....................................... 128/751 |

(List continued on next page.)

FOREIGN PATENT DOCUMENTS

| | | |
|---|---|---|
| 0 235 489 | 9/1987 | European Pat. Off. . |
| 2808911 | 3/1979 | Germany . |
| 9307621 | 7/1993 | Germany . |
| 4341734 | 9/1994 | Germany . |
| 2022421 | 12/1979 | United Kingdom . |
| 9400059 | 1/1994 | WIPO . |
| WO9400059 | 1/1994 | WIPO . |
| 9505123 | 2/1995 | WIPO . |

*Primary Examiner*—Michael Buiz
*Assistant Examiner*—Daphna Shai

[57] ABSTRACT

A surgical apparatus for cutting and storing sections of body tissue is provided comprising a housing having a handle assembly, an elongated outer tube extending from the handle assembly, and a cutting tube positioned within the outer tube and movable in response to actuation of the handle assembly between a retracted position and a distal position to cut body tissue. The cutting tube has a chamber formed therein for storing the cut tissue sections. A removable plug assembly is mounted on the proximal end of the cutting tube. A release lever is engagable with the trigger and is movable from a blocking position to a release position to release the trigger and allow the cutting tube to be removed from the outer tube. An anvil is positioned at a distal end of the outer tube for forcing each cut tissue section proximally into the chamber of the cutting tube as the cutting tube is advanced to cut the body tissue. A locking member is engagable with a rotation knob to prevent rotation of the knob.

33 Claims, 11 Drawing Sheets

U.S. PATENT DOCUMENTS

| | | |
|---|---|---|
| 4,674,501 | 6/1987 | Greenberg . |
| 4,722,338 | 2/1988 | Wright et al. . |
| 4,733,663 | 3/1988 | Farley . |
| 4,777,948 | 10/1988 | Wright ..................... 606/171 |
| 4,850,354 | 7/1989 | McGurk-Burleson et al. . |
| 4,955,887 | 9/1990 | Zirm . |
| 4,961,430 | 10/1990 | Sheahon . |
| 4,976,269 | 12/1990 | Mehl ........................................ 128/754 |
| 4,990,148 | 2/1991 | Worrick et al. ............................ 606/83 |
| 4,994,024 | 2/1991 | Falk . |
| 5,007,917 | 4/1991 | Evans . |
| 5,026,375 | 6/1991 | Linovitz et al. .......................... 606/79 |
| 5,031,634 | 7/1991 | Simon . |
| 5,106,364 | 4/1992 | Hayafuji et al. . |
| 5,174,300 | 12/1992 | Bales et al. . |
| 5,176,628 | 1/1993 | Charles et al. . |
| 5,176,699 | 1/1993 | Markham ............................... 606/206 |
| 5,226,910 | 7/1993 | Kaliyama et al. . |
| 5,250,065 | 10/1993 | Clement et al. . |
| 5,269,797 | 12/1993 | Bonati et al. . |
| 5,269,798 | 12/1993 | Winkler . |
| 5,273,519 | 12/1993 | Koros et al. . |
| 5,286,255 | 2/1994 | Weber . |
| 5,290,303 | 3/1994 | Pingleton et al. . |
| 5,308,358 | 5/1994 | Bond et al. ............................. 606/205 |
| 5,314,424 | 5/1994 | Nicholas ................................. 606/205 |
| 5,316,013 | 5/1994 | Striebel, II et al. ..................... 128/754 |
| 5,320,110 | 6/1994 | Wang . |
| 5,324,301 | 6/1994 | Drucker . |
| 5,327,896 | 7/1994 | Schmieding . |
| 5,336,238 | 8/1994 | Holmes et al. ......................... 606/208 |
| 5,374,277 | 12/1994 | Hassler ..................................... 606/170 |
| 5,375,608 | 12/1994 | Tiefenbrun et al. . |
| 5,385,570 | 1/1995 | Chin et al. . |
| 5,423,844 | 6/1995 | Miller . |
| 5,439,474 | 8/1995 | Li ............................................. 606/184 |
| 5,451,227 | 9/1995 | Michaelson ............................... 606/83 |
| 5,476,473 | 12/1995 | Heckele ................................... 606/171 |
| 5,496,347 | 3/1996 | Hashiguchi et al. .................... 606/205 |
| 5,507,774 | 4/1996 | Holmes et al. ......................... 606/205 |

SURGICAL CUTTING APPARATUS

This application is a continuation-in-part of U.S. patent application Ser. No. 08/416,268 filed Apr. 4, 1995, now abandoned, the contents of which are incorporated herein by reference.

BACKGROUND

1. Technical Field

This application relates to a surgical cutting instrument, and more particularly to a surgical cutting instrument having a chamber for storing the cut tissue portions.

2. Background of Related Art

Surgical instruments for cutting body tissue are well known. One type of instrument has a pair of scissors type jaws in which either both jaws move or one jaw moves relative to the other fixed jaw in a scissors like fashion, i.e. at an angle to the longitudinal axis of the instrument. An example of this scissors type instrument is disclosed in U.S. Pat. No. 4,994,024 to Falk. Another type of cutting instrument, especially useful in orthopedic procedures for cutting hard tissue or bone, has a cutting blade which is slidable longitudinally in either a distal or proximal direction to sever the body portion. Examples of this type of instrument are disclosed in U.S. Pat. No. 5,106,364 to Hayafuji et al., U.S. Pat. No. 4,850,354 to McGurk-Burleson et al., U.S. Pat. No. 5,226,910 to Kajiyama et al., and U.S. Pat. No. 4,282,884 to Boebel.

It is also recognized that as these cutting instruments dissect the body tissue, it is advantageous to remove the tissue portions as they are dissected or to store the dissected tissue portions in the instrument. This is especially the case in endoscopic surgical procedures. Endoscopic (minimally invasive) surgical procedures are performed under visualization through either small access ports or directly through small incisions in the body. Therefore, if the dissected body tissue is not removed as it is dissected, the instrument needs to be withdrawn from the surgical site each time a tissue portion is cut, the tissue portion needs to be manually removed from the instrument, and then the instrument needs to be reinserted to the surgical site. These steps need to be repeated until the entire tissue section is removed. This repeated re-insertion of the instrument can be very time consuming, and therefore more expensive, especially in endoscopic procedures, because the surgery is being performed at a remote surgical site. The repeated insertion can also cause complications in endoscopic procedures where access to the surgical site is difficult such as in endoscopic discectomy.

As noted above, the advantages attendant removing or storing the dissected body tissue portions are well known. One way of continuously removing the tissue portion as it is dissected is by utilizing suction. One example of the use of suction is disclosed in U.S. Pat. No. 4,589,414 to Yoshida et al. In Yoshida, a cutting member slides longitudinally in a distal direction to cut body tissue positioned in the opening in the instrument and the cut tissue is withdrawn through a suction channel in the inner tube. U.S. Pat. No. 5,007,917 to Evans discloses a rotatable cutting blade for cutting tissue and a suction tube for removing the tissue. The aforementioned patent to Falk discloses a vacuum extraction channel for use with a scissors type cutting instrument.

U.S. Pat. No. 4,282,884 to Boebel, identified above, has a storage chamber for the cut tissue. The punch assembly is slid in a proximal direction, and the punched out tissue portion is pressed into a tubular receiver member and stored therein. At the end of the procedure, the tissue portions can be removed from the receiver member.

The need exists for an improved cutting instrument for storing dissected tissue portions for removal at the end of the procedure. Such instrument would advantageously be configured to force the tissue sections into the storage chamber to prevent clogging and allow for maximum use of the space in the chamber. The instrument would also advantageously enable easy access and removal of the tissue sections at the end of the procedure.

SUMMARY

A surgical apparatus for cutting and storing sections of body tissue is provided comprising a housing having a handle assembly, an elongated outer tube extending from the handle assembly, and a cutting tube positioned within the outer tube and movable in response to actuation of the handle assembly between a retracted position and a distal position to cut body tissue. The cutting tube has a chamber formed therein for storing the cut tissue sections. A plug or end cap assembly is mounted at the proximal end of the cutting tube and is removable therefrom after the cutting tube is removed from the outer tube to access the cut tissue sections. An anvil may be positioned at a distal end of the outer tube for forcing each cut tissue section proximally into the chamber of the cutting tube as the cutting tube is advanced to cut the body tissue. The outer tube preferably has a window at a distal end to receive the body tissue and the anvil is positioned distally of the window.

The plug assembly preferably includes a plug and a retaining member having a pair of ears extending into a pair of notches in the cutting tube such that pulling on the plug when the cutting tube is positioned within the outer tube cams the ears further into engagement with the notches to prevent removal of the plug.

The handle assembly preferably includes a trigger movable from a first position to a second position to advance the cutting tube and further movable to a release position to enable release of the cutting tube. A release lever may be provided which is engagable with the trigger and movable from a first engaged position to a release position to enable the trigger to move to its release position to enable removal of the cutting tube from the outer tube.

In a preferred embodiment, a rotating knob rotates the elongated body portion i.e., the outer tube and cutting tube, about its longitudinal axis. A locking member may also be provided which is engagable with the rotating knob to prevent rotation thereof.

BRIEF DESCRIPTION OF THE DRAWINGS

Various embodiments are described herein with reference to the drawings, wherein.

DETAILED DESCRIPTION OF PREFERRED EMBODIMENTS

Figures 1, 1A:
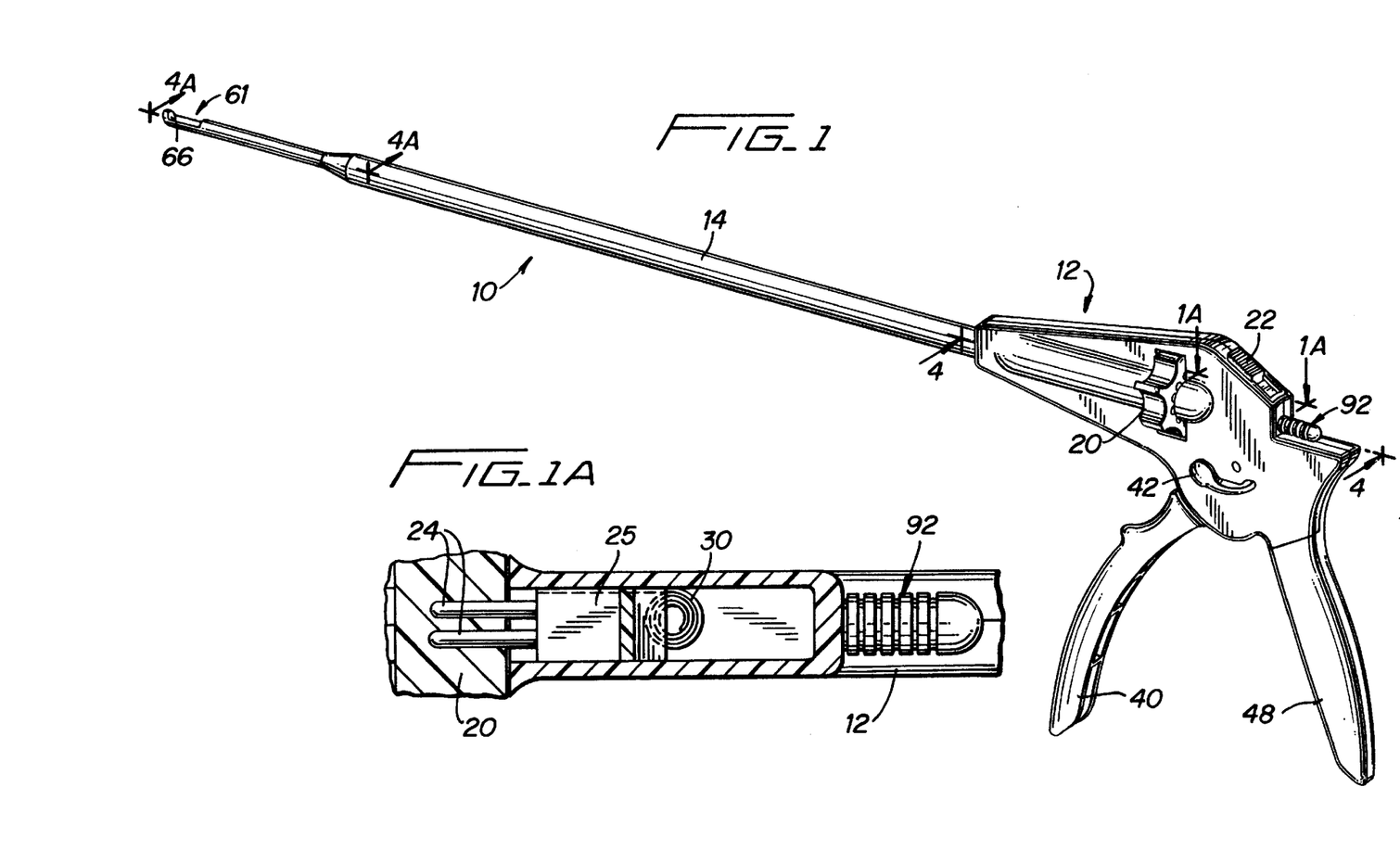
FIG. 1 is a perspective view showing the surgical cutting apparatus with the cutting tube in the retracted position.
FIG. 1A is an enlarged cross-sectional view taken along lines 1A—1A of FIG. 1 showing the engagement of the locking button with the rotation knob to prevent rotation of the outer tube.

Referring now to the drawings and in particular to FIGS. 1 and 1A, the surgical apparatus, designated generally by reference numeral 10, is illustrated for cutting body tissue. The apparatus has an elongated outer tube or endoscopic portion 14 extending from housing or handle assembly 12. Outer tube 14 is dimensioned and configured for either insertion through a trocar cannula or through a small incision in the body tissue. Slidably positioned within outer tube 14 is an elongated hollow inner cutting tube 16. Cutting tube 16 is advanced distally upon actuation of handle assembly 12 to cut body tissue positioned in window 61 of outer tube 14. An anvil 66, positioned at a distal end of the outer tube 14, forces the severed body tissue portion rearwardly inside the cutting tube 16. In this manner, the apparatus can be inserted inside the body and the cutting tube 16 repeatedly advanced to cut body tissue with the anvil 66 forcing the cut tissue sections proximally inside the cutting tube to enable storage of a plurality of tissue portions. The cutting tube 16 can subsequently be easily separated from the apparatus to access and remove the individual tissue sections stored therein. This is achieved by removal of the plug assembly, which includes a plug 92 and a plug retainer 90, from the proximal end of cutting tube 16 in the manner described below.

A release lever 42 is mounted on the handle assembly 12 and cooperates with the trigger 40 to enable movement of the trigger 40 to a release position so the cutting tube 16 can be removed from the apparatus. The release lever 42 is shown in FIG. 1 in the engaged (blocking) position. Also shown in FIG. 1 is rotation knob 20 for rotating the outer tube 14 (and inner cutting tube 16) about its longitudinal axis. A locking button 22 is engagable with the rotation knob 20 to lock the knob 20 and prevent rotation of the tubes 14, 16. The locking button 22 and the release lever 42 are discussed in detail below.

Figures 3, 3A:
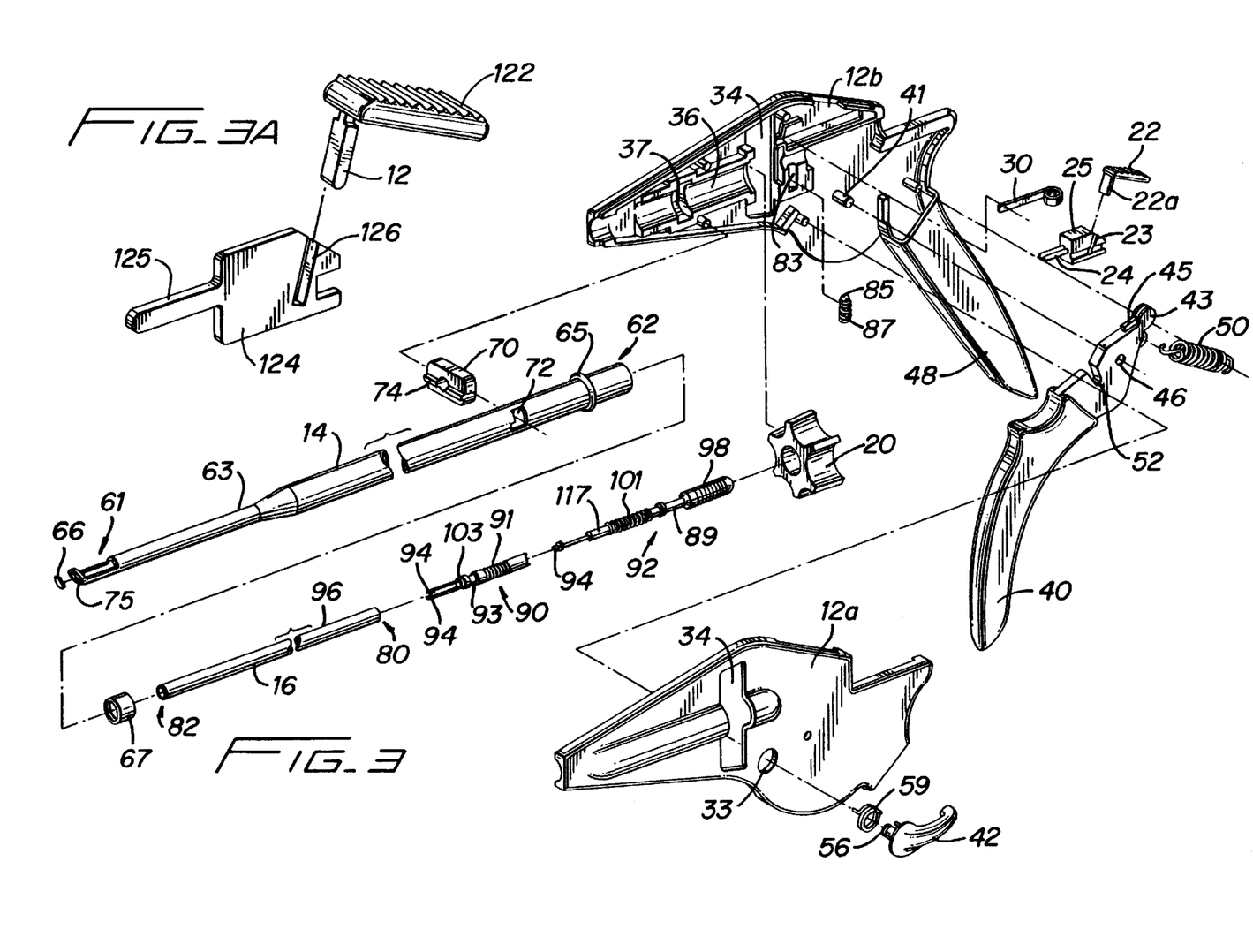
FIG. 3 is an exploded perspective view of the apparatus of FIG. 1.
FIG. 3A is an exploded perspective view of an alternate embodiment of the mechanism for locking the rotation knob.
Figures 6, 6A:
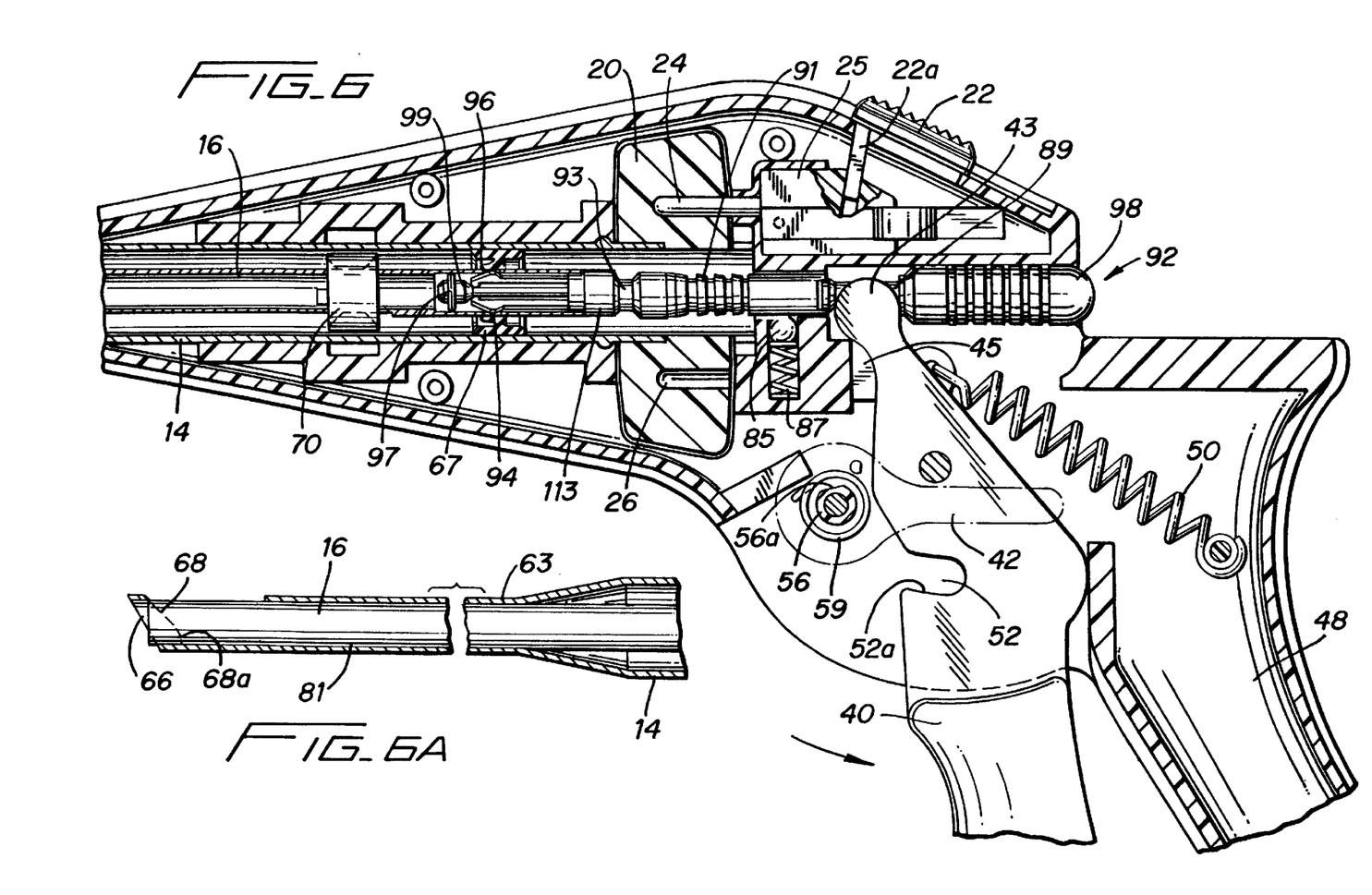
FIG. 6 is a cross-sectional view similar to FIG. 4 showing the trigger in the proximal position and the cutting tube in the advanced (distal) position to cut body tissue.
FIG. 6A is a cross-sectional view similar to FIG. 4A showing the cutting tube in the advanced position.

Turning now to the individual components of the apparatus 10, and first to the handle assembly 12 as illustrated in FIGS. 1 and 3, handle assembly 12 is composed of two housing halves 12a, 12b welded together or attached by other known methods. Trigger 40 is pivotably mounted to housing halves 12a, 12b via mounting pin 41 extending through opening 46. Trigger 40 is movable between three positions. In the first (initial) position shown in FIG. 4, the cutting tube 16 is in the retracted position. In the second position as shown in FIG. 6, trigger 40 is moved towards stationary grip 48 to advance the cutting tube 16 distally. In the third position, trigger 40 is moved to a distal release position shown in FIG. 8 which enables the cutting tube 16 to be withdrawn from the outer tube 14 in the manner described below.

In the initial position of trigger 40, spaced apart projecting fingers 43 engage rod portion 89 of the plug assembly, which is mounted to the cutting tube 16, such that proximal (counterclockwise) movement of trigger 40 in the direction of the arrow of FIG. 6, slides cutting tube 16 distally to cut the tissue positioned in window 61 (FIG. 6A).

Figures 4, 4A:
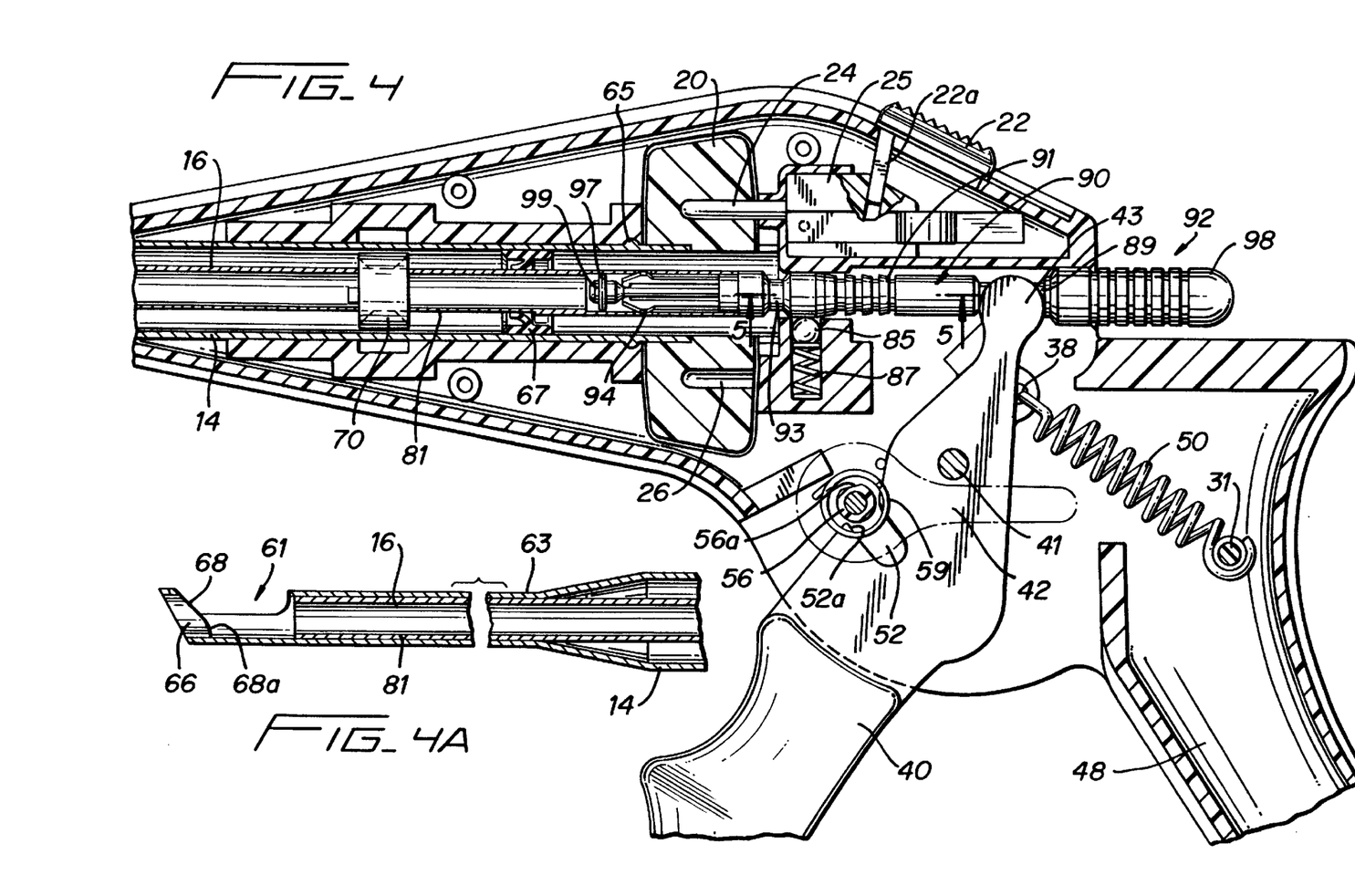
FIG. 4 is a cross-sectional view taken along lines 4—4 of FIG. 1 showing the trigger in the initial position and the cutting tube in the retracted position.
FIG. 4A is a cross-sectional view taken along lines 4A—4A of FIG. 1 showing the cutting tube in the retracted position.

Trigger 40 is normally biased to the third position by extension spring 50; however it is prevented from moving to this position by lever mounting shank 56 when release lever 42 is in the blocking position. Therefore, when release lever 42 is in its normal blocking position of FIG. 4, trigger 40 is essentially biased by extension spring 50 to the first position. When release lever 42 is pivoted to its release position of FIG. 8, trigger 40 is no longer blocked and can spring forward to its third position. As shown in FIG. 4, one end of extension spring 50 is mounted on post 31 of stationary grip 48 and the other end extends through aperture 38 in trigger 40. Stop 45 limits the pivotal movement of trigger 40.

Figure 8:
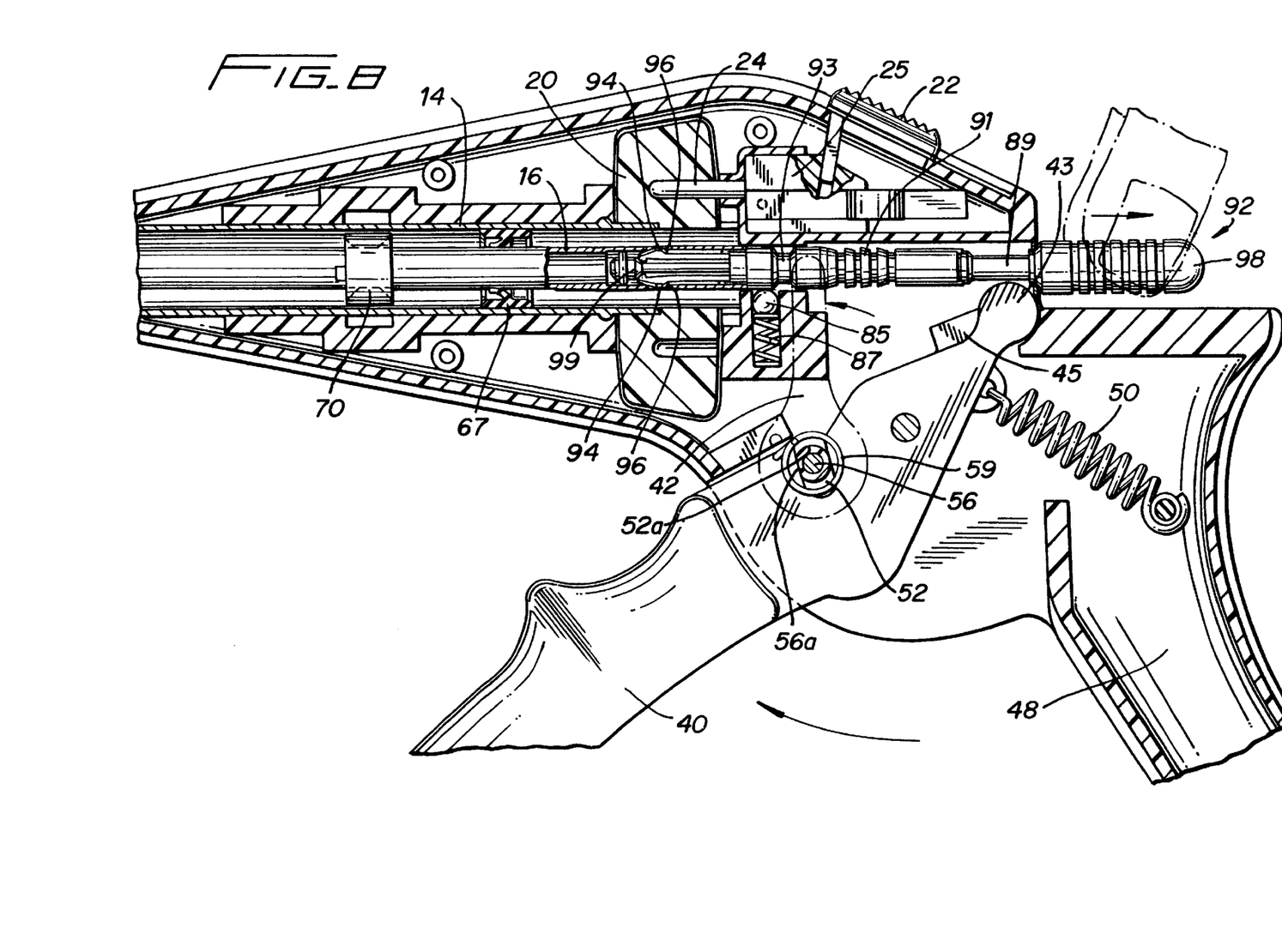
FIG. 8 is a cross-sectional view similar to FIG. 4 showing the release lever in the release position, the trigger in the distal release position and the plug assembly being pulled rearwardly to remove the cutting tube.

The release lever 42 blocks movement of trigger 40 due to mounting shank 56. Mounting shank 56 extends through opening 33 in handle housing half 12a. Torsion spring 59 biases lever 42 to the trigger blocking position shown in FIGS. 4 and 6. In this blocking position, trigger 40 is prevented from moving to its distal position by mounting shank 56 because trigger notch 52 of trigger 40 abuts curved surface 56b of shank 56. This prevents the removal of cutting tube 16 from outer tube 14 since projecting fingers 43 remain engaged in rod portion 89 of the plug assembly. When release lever 42 is pivoted to its upward release position as shown in FIG. 8, trigger notch 52 can bypass mounting shank 56 due to the alignment of flat 56a of mounting shank 56 with surface 52a of notch 52. Consequently, trigger 40 springs forward to the release position so that projecting fingers 43 are out of engagement with the plug assembly to allow removal of the cutting tube 16.

Turning now the outer tube 14 and with reference to FIGS. 1, 3 and 4, outer tube 14 has an open distal end 60 to mount anvil (tissue engaging member) 66, a window 61 to receive the body tissue to be cut, and a proximal end portion 62 positioned within longitudinal recess 36 formed by housing halves 12a, 12b. Lip 65 helps retain outer tube 14 in handle assembly 12. Central bore 64 of outer tube 16 is dimensioned to slidably receive cutting tube 16. A cylindrically shaped seal 67 is positioned inside the outer tube 14 and surrounds the cutting tube 16 to restrict the egress of gas through the gap between the outer tube 14 and cutting tube 16 if the body cavity is insufflated during the procedure. Clearly, other types of seals to restrict gas flow are also contemplated.

The outside diameter of the outer tube 14 is preferably about 10 mm and preferably is tapered as shown at portion 63 to an outside diameter of about 5 mm, although other dimensions are clearly contemplated. Anvil 66 is mounted at distal end 60 of outer tube 14 via dovetail fitting 66a (FIG. 4B) and has an angled surface 68 corresponding to the angled distal tip 75 of outer tube 12 (see FIGS. 4A and 4B). The angled distal tip 75 facilitates manipulation and use of the apparatus as it can more readily be hooked behind the target tissue. Angled surface 68 of anvil 66 also has a straight portion 68a which helps force the cut tissue sections proximally into cutting tube 16 when the cutting tube 16 is advanced. Angled surface 68 preferably forms an angle with respect to the central longitudinal axis of outer tube 14 ranging from approximately 90 degrees to about 140 degrees, and preferably an angle R of 130° degrees. Alternatively, other angles, such as a 90° angle can be utilized.

An orientation plate 70 is positioned within outer tube 12 and extends through slots 72 to sit within cavity 37 of handle assembly 12. D-shaped central opening 74 is dimensioned to receive cutting tube 16 therethrough.

Cutting tube 16, as shown in FIGS. 3, 4, 4A and 4B has an open proximal end 80 and an open distal end 82. The distal end 82 is shown having a circumferential straight cutting edge, however alternately an angled edge can be provided either integrally formed with the cutting tube 16 or a separate element attached thereto. A plurality of cutting teeth can also alternatively be provided. The cutting tube 16 has an axial bore 86 extending the length thereof which forms a chamber for storing the individual tissue portions as they are cut. Anvil 66 forces the cut tissue sections rearwardly into axial bore 86 to create space in the cutting tube 16 for receiving the next cut tissue section when cutting tube 16 is once again advanced to cut tissue.

Cutting tube 16 has a flattened bottom surface 81 which sits on the flat bottom surface of D-shaped opening 74 of orientation plate 70. This prevents lateral movement and rotation of the cutting tube as well as aligns the cutting tube 16 inside outer tube 14.

Referring to FIGS. 3, 4, 5 and 5A, plug assembly (end cap assembly) is mounted on the proximal end 80 of cutting tube 16 and includes a plug 92 and a plug retainer 90 for preventing removal of plug 92. Plug retainer 90 is seated in the proximal portion of axial bore 86, is spring biased distally by compression spring 101 mounted on tubular portion 117 of plug 92, and has a pair of spaced apart ears 94 seated in a pair of notches 96 formed in the cutting tube 16. Ears 94 are supported by shank 103 which has an outer diameter almost equal to the inner diameter of the cutting tube 16 to enable frictional engagement of shank 103 and cutting tube 16 to stabilize the cutting tube 16. The proximal end of cutting tube 16 abuts surface 107 of cylindrical portion 113 of plug retainer 90. Proximal extensions 116 are seated within recesses 118 formed in a head portion 112 of plug 92.

Figure 9:
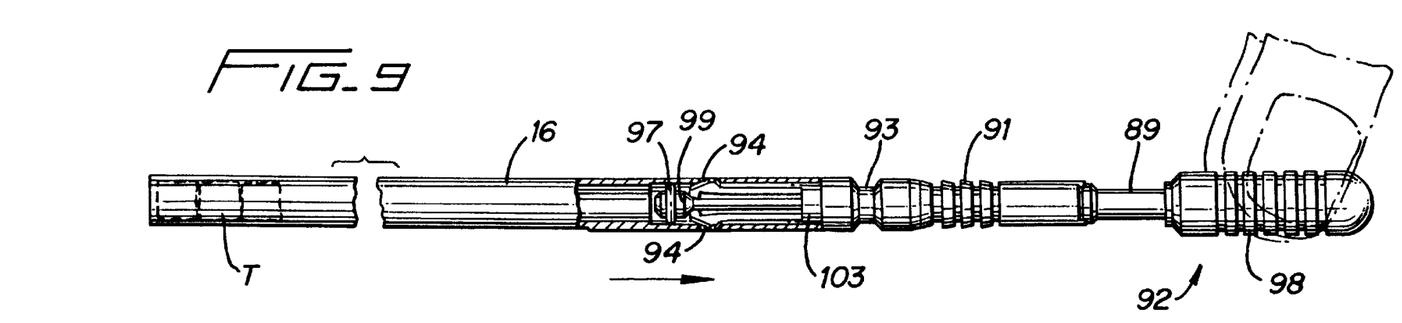
FIG. 9 is a side view in partial cross-section illustrating grasping of the plug to remove the cutting tube and plug assembly from the outer tube.

Plug 92 has a knurled gripping surface 98 at its proximal end and a cam nose 99 at its distal end. O-ring 97 is seated in a circumferential recess of cam nose 99 to provide a seal to prevent the egress of insufflation gas through the cutting tube 16 if the apparatus is used in a procedure performed under insufflation. Other seals can also be utilized. In the initial position, notches 111 of ears 94 rest on camming surface 105 of camming nose 99 and the ears 94 extend through notches 96 of cutting tube 16 to connect the plug assembly to the cutting tube 16. This is best shown in FIG. 4. If the plug 92 is gripped by its knurled surface 98 and pulled proximally, cam nose 99 will be pulled proximally between ears 94 to enable camming surface 105 to cam the ears 94 further outwardly into locking engagement with notches 96 of cutting tube 16 as shown in FIG. 8 and 9. This enables the cutting tube 16 to be removed. Note that this locking engagement prevents removal of plug 92 from cutting tube 16 if knurled surface 98 is pulled. Thus, the ears also function to provide a locking device to prevent inadvertent disengagement of the plug assembly from the cutting tube 16.

Figure 10:
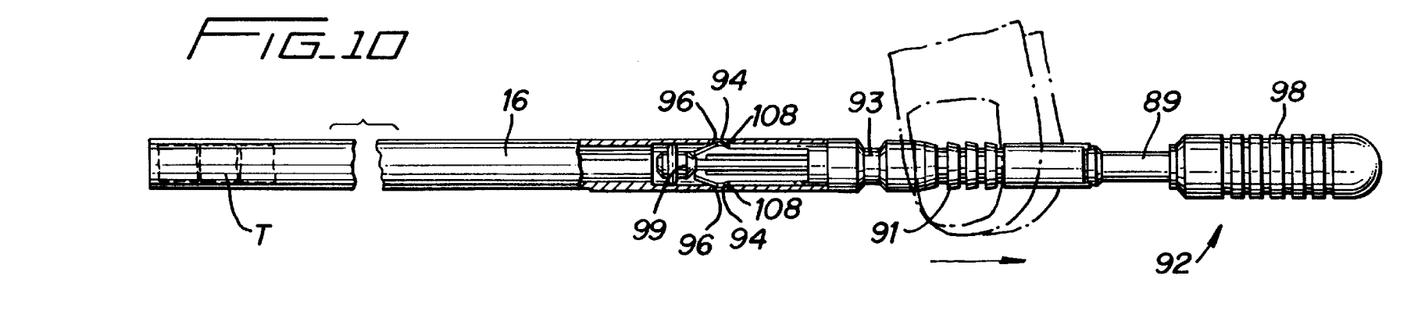
FIG. 10 is a side view in partial cross-section illustrating grasping of the plug retainer to remove the plug assembly from the cutting tube.
Figure 11:
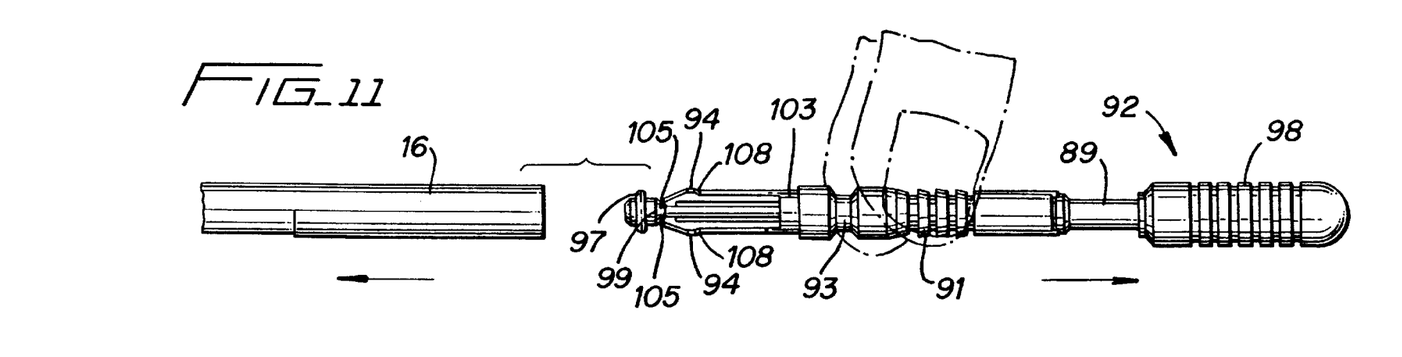
FIG. 11 is a side view illustrating removal of the plug assembly from the cutting tube.

The plug assembly can be removed from cutting tube 16 to access the tissue stored therein only when knurled gripping surface 91 of the plug retainer 90 can be grasped. This occurs only when the release lever 42 has been rotated to its release position to disengage the projecting fingers 43 of trigger 40 from rod portion 89, and the cutting tube 16 is withdrawn from the outer tube 14 as shown in FIG. 10. Only when this occurs can knurled surface 91 be accessed. When plug retainer 90 is pulled proximally in the direction of the arrow, the ears 94 can slide out of notches 96 as camming release surfaces 108 are forced inwardly by the wall 115 of cutting tube 16 adjacent the notches 96 and plug retainer 90 (and attached plug 92) can be removed from the outer tube 14 as shown in FIG. 11. The tissue sections T can then be removed and organized for pathology.

Figure 7:
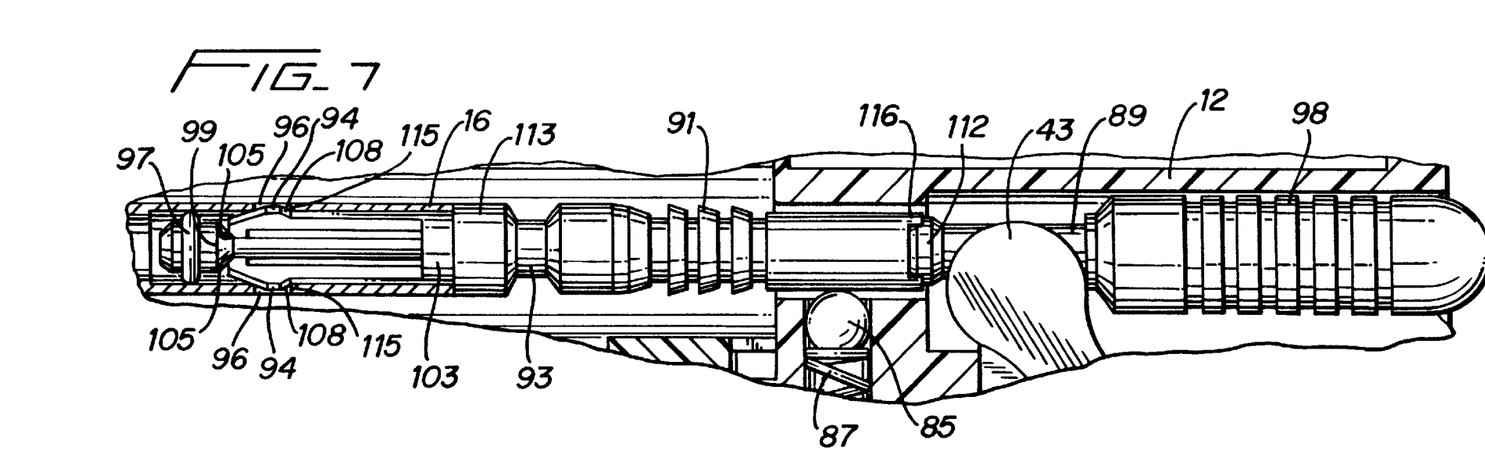
FIG. 7 is an enlarged cross-sectional view corresponding to the position of the trigger and cutting tube in FIG. 6.

As best shown in FIG. 7, recess 93 in the plug assembly is configured to receive detent sphere 85 when the trigger 40 is in the release position. Sphere 85 is seated within recess 83 in housing half 12b and is spring biased by compression spring 87 to snap into engagement with recess 93 in plug retainer 90 to prevent the cutting tube 16 from slipping out of outer tube 14 when the trigger 40 is in the release position (see FIG. 7A). This engagement also provides a tactile feel to the user that the cutting tube 16 is released for withdrawal from outer tube 14 as well as when the cutting tube 16 has been properly re-inserted into the outer tube 14 of the apparatus.

Figures 2, 2A:
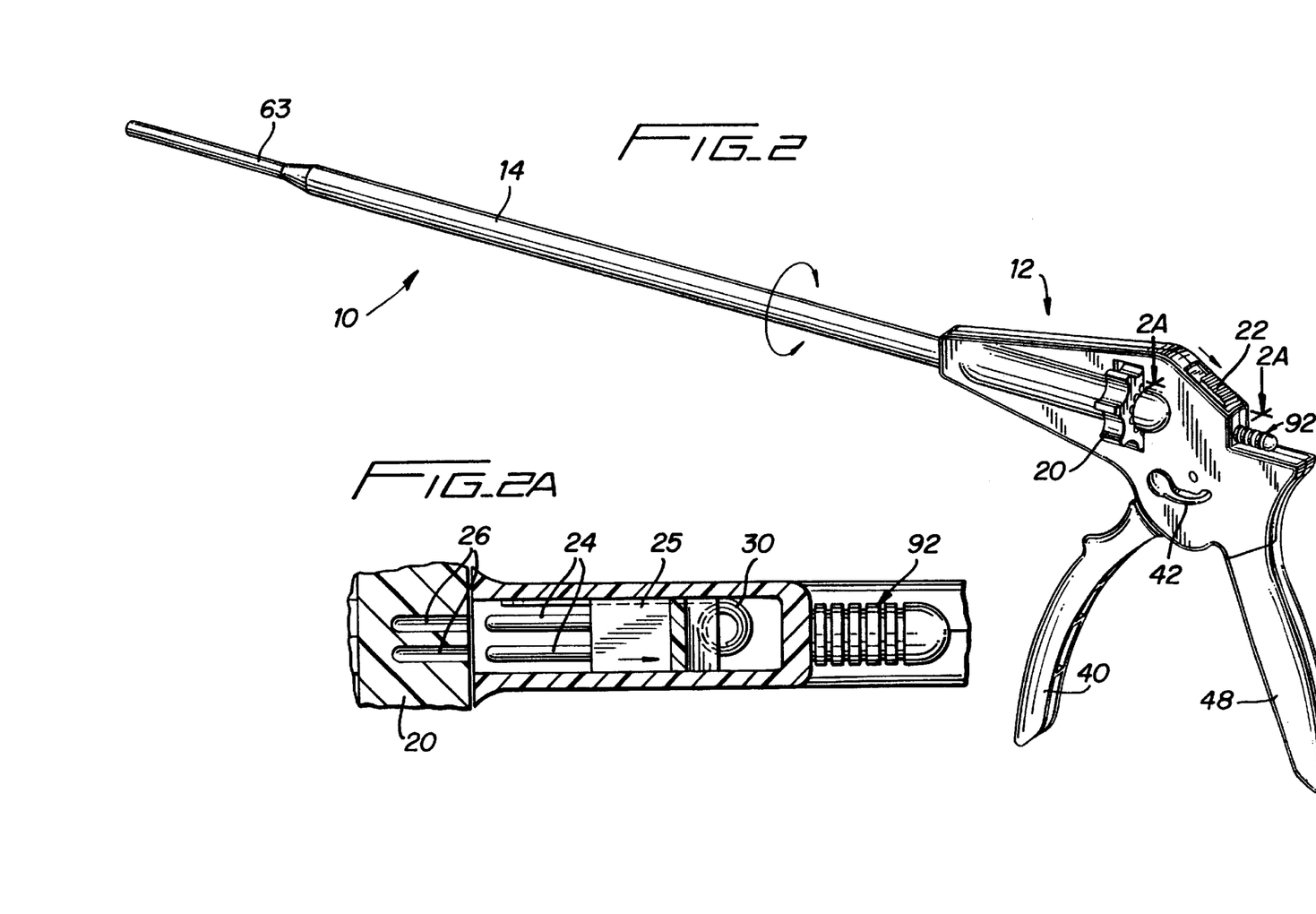
FIG. 2 is a perspective view of the apparatus of FIG. 1 showing the locking button in the release position and rotation of the outer tube.
FIG. 2A is an enlarged cross-sectional view taken along lines 2A—2A of FIG. 2 illustrating the locking button in the release position disengaged from the rotation knob.

Turning now to the rotation knob 40 and with reference to FIGS. 1 and 3, as mentioned above, rotation knob 20 extends through cutout 34 in housing halves 12a, 12b and is mounted to outer tube 14 to rotate outer tube 14 about its longitudinal axis. Rotation of outer tube 14 causes rotation of cutting tube 16 due to orientation plate 70 which rotates with outer tube 14. Leg 22a of rotation locking button 22 is seated within recess 23 of mounting block 25, slidably mounted on handle assembly 12, and spring biased to the locking position by spring 30. Locking button 22 is shown in FIGS. 1 and 1A in the locking position. In this locking position, the pair of locking fingers 24 of mounting block 25 engage a pair of recesses 26 in rotation knob 20 to thereby prevent rotation of knob 20. When it is desired to rotate outer tube 14 to change the orientation of the window 61, locking button 22 is slid proximally in the direction of the arrows of FIGS. 2 and 2A. This slides mounting block 25 proximally to release the locking fingers 24 from recesses 26 and allow free rotation of rotation knob 20. When locking button 22 is released by the user, it springs back into the locking position under the biasing force of spring 30.

An alternate embodiment of a rotation knob locking mechanism is shown in FIG. 3A. Locking button 122 has a mounting leg 123 seated within recess 126 in locking plate 124. Locking plate 124 has a single integral extension 125 which engages a single recess in the rotation knob to prevent rotation.

Figure 4B:
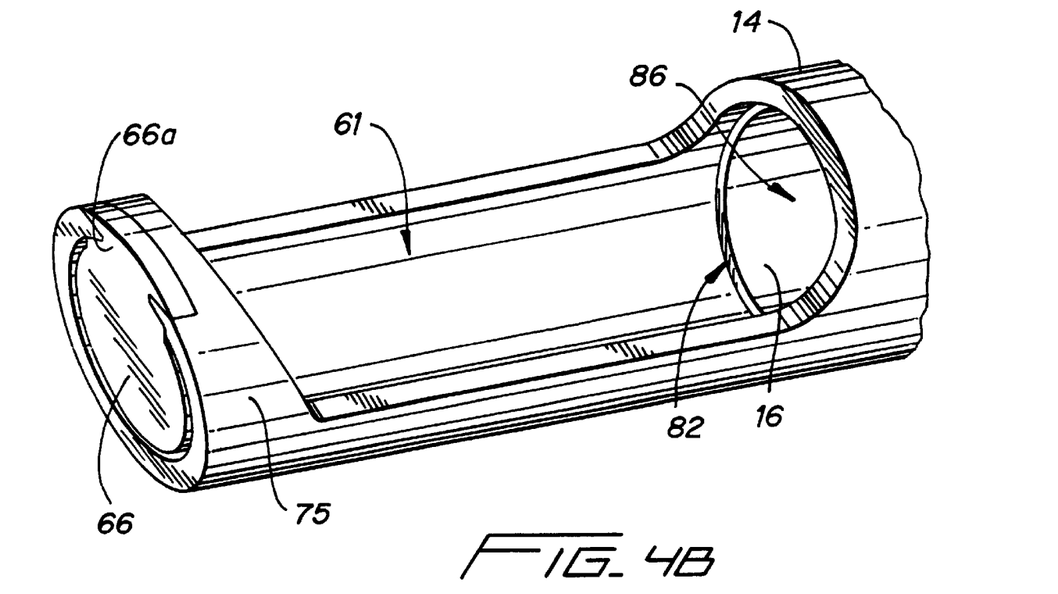
FIG. 4B is an enlarged perspective view of the distal end of the apparatus of FIG. 1 showing the cutting tube retracted inside the outer tube.
Figures 5, 5A:
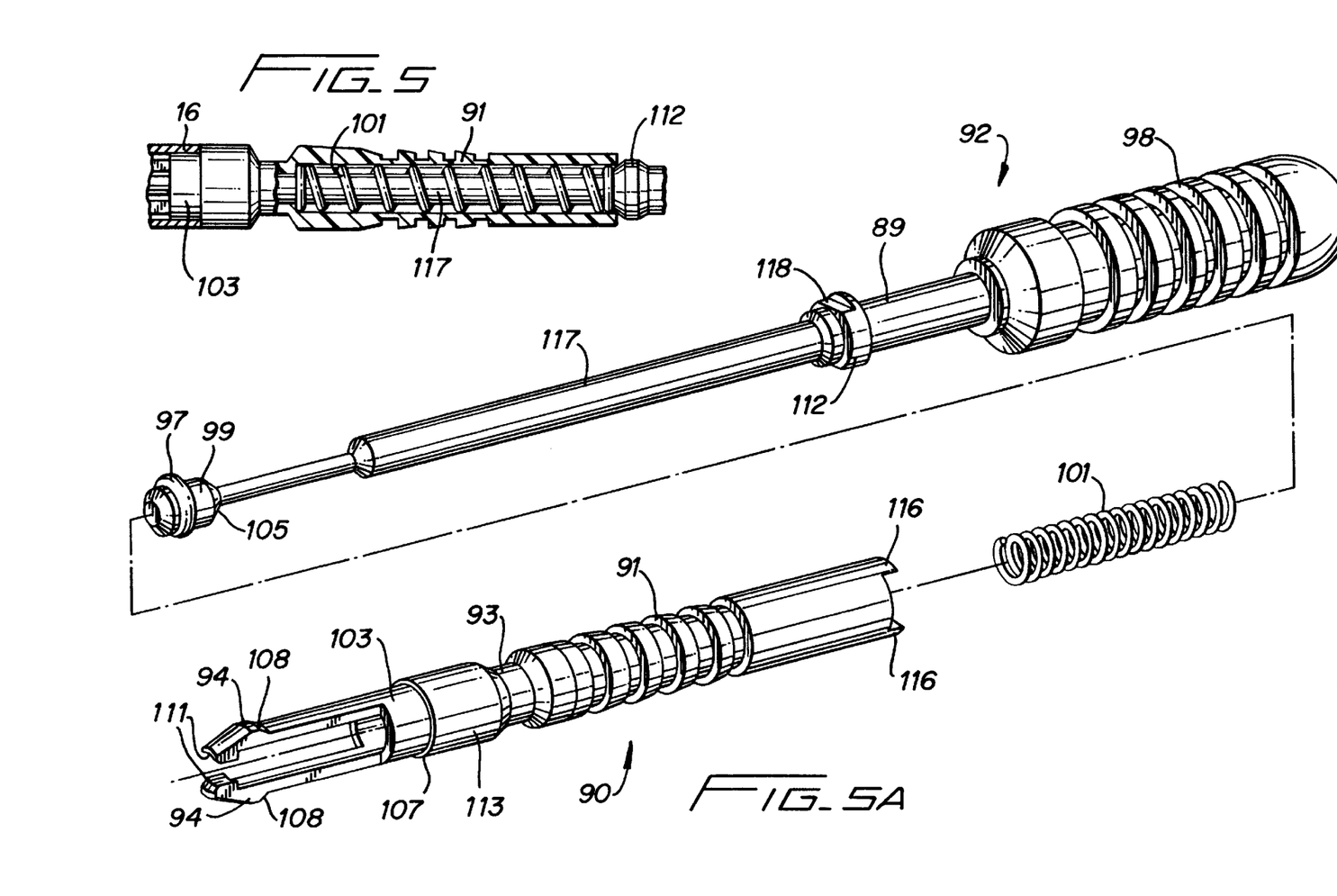
FIG. 5 is an enlarged side view in partial cross-section of a portion of the plug assembly.
FIG. 5A is an enlarged exploded perspective view of the plug assembly.

In operation, with reference initially to FIGS. 4, 4A and 4B, trigger 40 is initially spaced from stationary grip 48 with projecting fingers 43 engaging rod portion 89 of plug 92. As shown, cutting tube 16 is in the proximal (retracted) position and release lever 42 is in the blocking position parallel to the longitudinal axis of the tubes 14, 16.

Figure 6B:
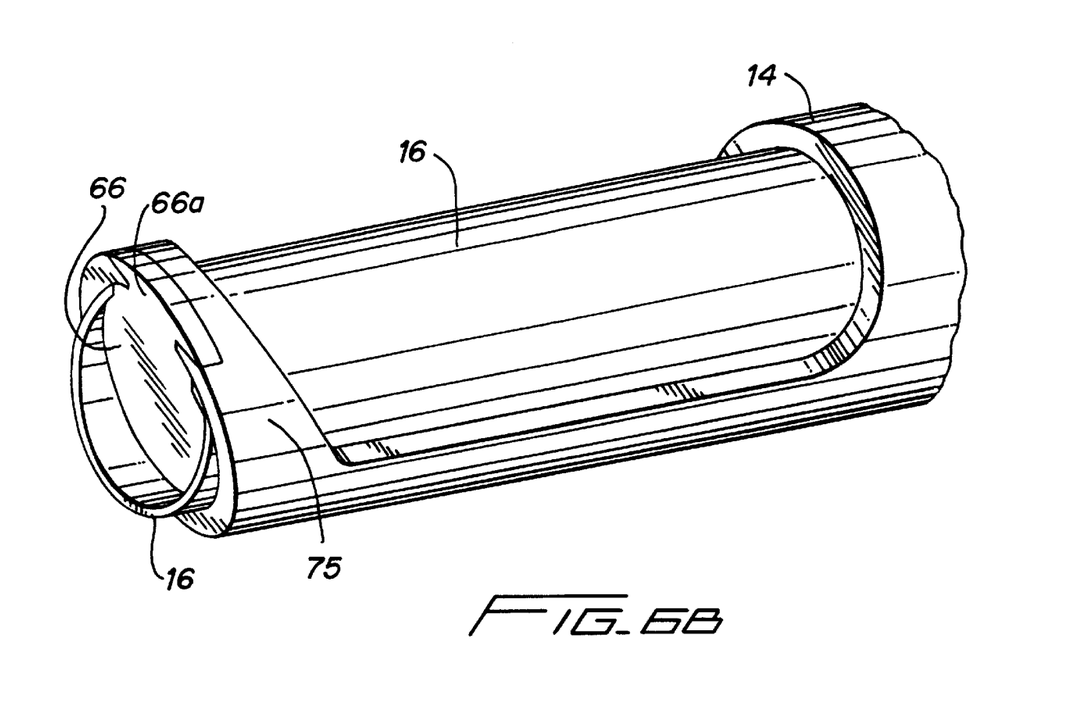
FIG. 6B is an enlarged perspective view of the distal end of the apparatus of FIG. 1 showing the cutting tube in the advanced position to cut body tissue.

The apparatus is inserted into the body, either through a cannula or directly through a small incision, and the outer tube 14 is placed adjacent the surgical site such that the tissue to be severed is seated within window 61. If the user needs to re-orient the window 61, locking button 22 is slid proximally to disengage locking fingers 24 from the recesses 26 in the rotation knob 20. Locking button 22 is held by the user in this proximal position and the rotation knob is turned to rotate outer tube 14 (and window 61) to the desired position. Once the tissue is properly seated, trigger 40 is actuated by squeezing it towards stationary grip 48 to advance cutting tube 16 distally towards anvil 66 as shown in FIGS. 6, 6A and 6B. The cutting edge of the cutting tube 16 passes through the window 61 to pierce and dissect the body tissue seated therein. As the cutting tube 16 passes over anvil 66, angled surface 68 and straight surface 68a enter the hollow interior of the cutting tube 16, and force the dissected tissue proximally into the cutting tube 16. After dissection, trigger 40 is released, returning cutting tube 16 to the proximal position of FIG. 4A. Note that plug 92 cannot be removed from the cutting tube 16 due to the engagement of ears 94 with the notches 96 of cutting tube 16.

The user can then once again squeeze trigger 40 to advance cutting tube 16 to dissect another portion of the body tissue positioned in window 61. As the cutting tube 16 advances to its distalmost position, anvil 66 once again forces the dissected tissue rearwardly (proximally) into cutting tube 16. The cutting tube 16 can be repeatedly advanced and retracted in this manner to dissect the entire desired portion of body tissue, with the anvil 66 advantageously forcing the body tissue sections proximally to provide room for the next body tissue portion. FIG. 9 illustrates a plurality of body tissue sections T positioned within cutting tube 16.

Note that when trigger 40 and cutting tube 16 are in the position of FIGS. 4 and 4A, the cutting tube 16 cannot be removed from outer tube 14. If the user grasps gripping surface 98 of plug 92 in an attempt to remove cutting tube 16, projecting fingers 43 of trigger 40 will block removal of the cutting tube 16. Also in the position of FIGS. 4 and 4A, the plug 92 cannot be removed from the cutting tube 16 because ears 94 engage notches 96 of cutting tube 16 and if the user pulls on gripping surface 98, the camming nose 99 of plug 92 will cam the ears further into engagement with notches 96.

After use, to remove the tissue from the chamber 86 of cutting tube 16, release lever 42 is rotated counterclockwise to the position of FIG. 8 so that flat 56a of mounting shank 56 is in alignment with surface 52a of trigger notch 52. Consequently, notch 52 rides over mounting shank 56 to allow trigger 40 to spring forward to its distal release position under the force of extension spring 50. In this distal release position, the projecting fingers 43 are disengaged from notch 89 in the plug 92. Thus, when the user grasps gripping surface 98 of plug 92 and pulls proximally, the entire cutting tube 16 is withdrawn from the outer tube 14 through the opening in proximal end 62 as the ears 94 of plug retainer 92 engage notches 96 in cutting tube 16.

Figure 12:
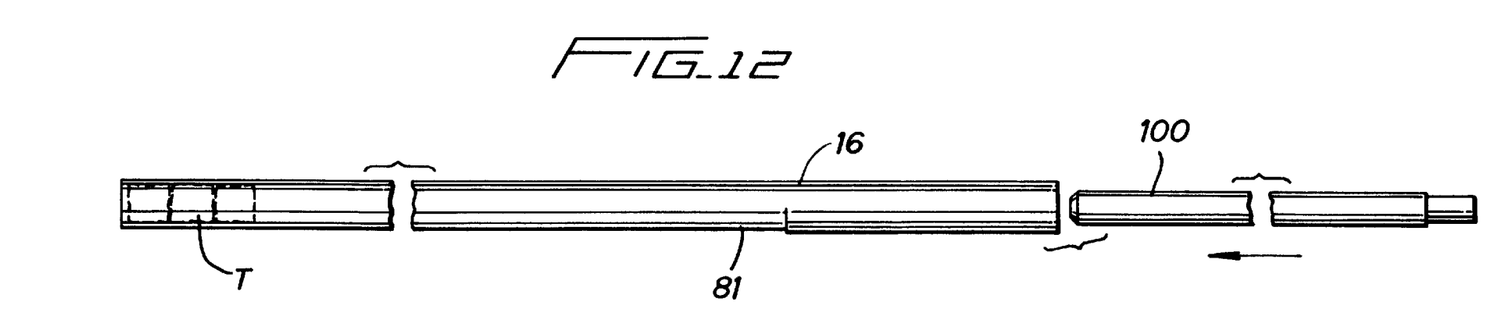
FIG. 12 is a side view showing the direction of insertion of the plunger into the cutting tube to remove the tissue sections contained therein.
Figure 13:
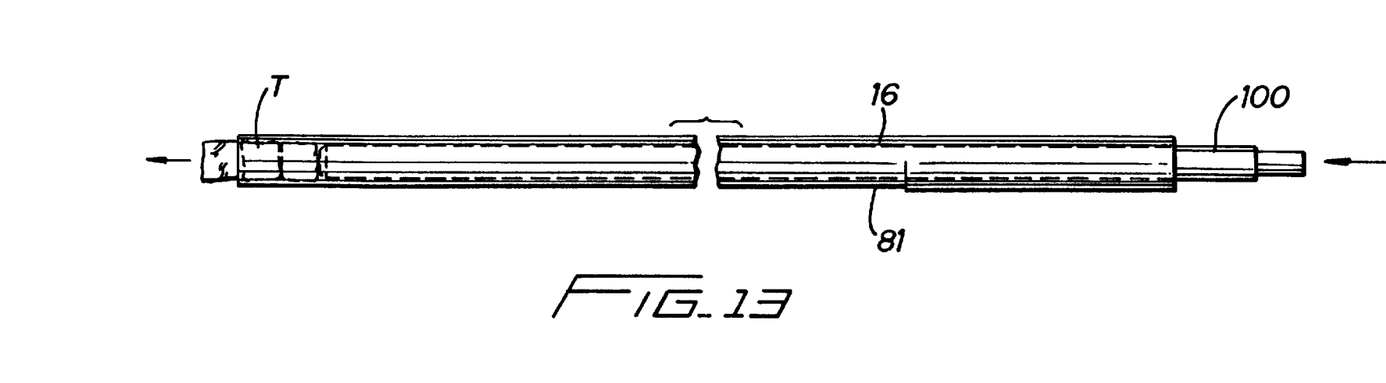
FIG. 13 is a side view showing the plunger inserted into the cutting tube to force the tissue sections out of the distal end.

After the cutting tube 16 has been removed as shown in FIG. 9, to access the tissue portions, gripping surface 91 of plug retainer 90 is grasped and pulled proximally (FIG. 10). This removes the plug 92 and plug retainer 90 from cutting tube 16 since the ears 94 are cammed closed by wall 115 adjacent notches 96 so they can slide out of notches 96. FIG. 11 illustrates the plug assembly separated from the cutting tube 16. The tissue sections T can then be removed from cutting tube 16 and arranged in a manner similar to their configuration prior to dissection to assist in examination and testing of the tissue. FIGS. 12 and 13 illustrate one method of removing the tissue sections T in which plunger 100 is inserted through the open proximal end 80 of cutting tube 16 to force the tissue sections out of the open distal end 82.

Figure 7A:
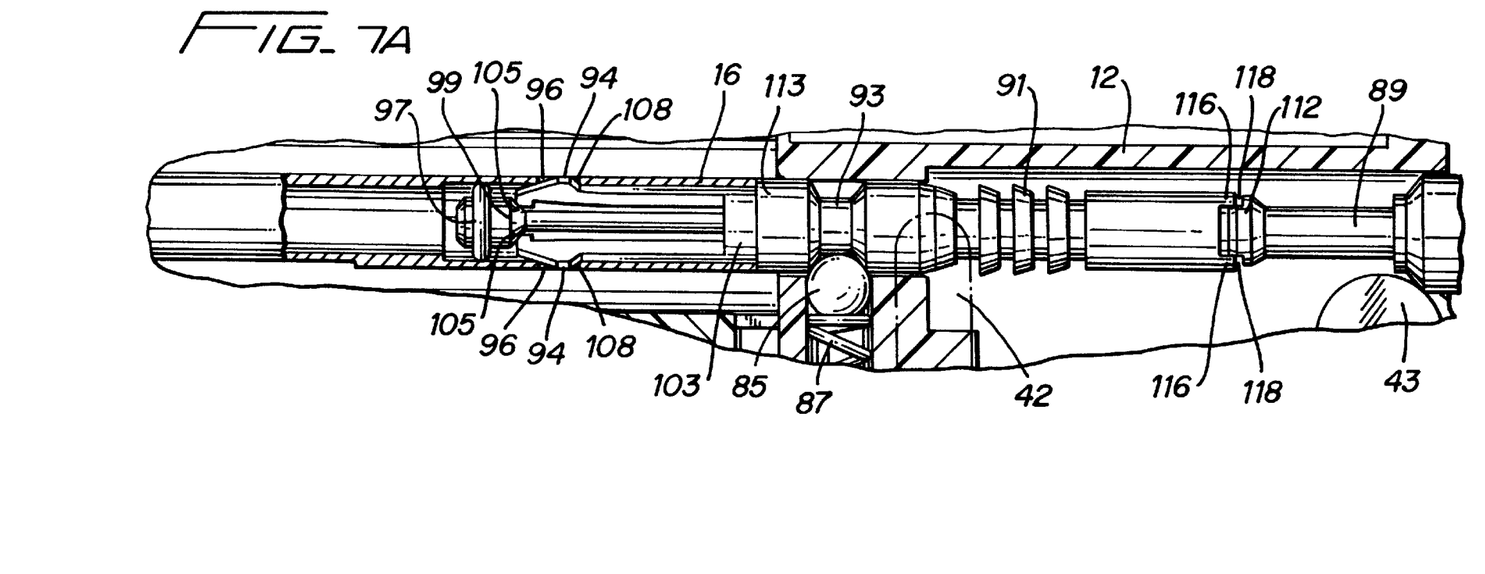
FIG. 7A is an enlarged cross-sectional view corresponding to the position of the trigger and cutting tube when the trigger is moved to the release position.

For subsequent use of the instrument, cutting tube 16 is inserted through the opening in proximal end 62 of outer tube 14 until the user feels the engagement of detent sphere 85 with recess 93 as in FIG. 7A. Trigger 40 is then squeezed towards stationary grip 48, causing release lever 42 to rotate clockwise over center, under the force of torsion spring 59, to its original position of FIG. 4 enabling projecting fingers 43 to engage rod portion 89 of plug 92. The cutting tube 16 can then be actuated by squeezing trigger 40 in the manner described below for reuse.

The apparatus can be entirely disposable and can be discarded after use. It can also be partially disposable with some parts discarded e.g. the cutting tube and plug assembly, and the remaining parts, e.g. the handle assembly, reused. Alternatively, the apparatus can be composed of suitable materials to enable re-sterilization of the instrument parts for subsequent reassembly and reuse. The apparatus 10 can be packaged in a kit with several cutting tubes (and plug assemblies).

The instrument 10 can be used to dissect tissue in a variety of surgical procedures. For example, in endoscopic discectomy procedures, the instrument can be inserted into the disc space to quickly dissect portions of the disc. The cutting tube can then be removed in the manner described above and the tissue sections removed and analyzed. The instrument can also be used as a ronguer for cutting and storing sections of bones in other surgical procedures.

It will be understood that various modifications may be made to the embodiments disclosed therein. For example, a cutting tube having teeth or having other cutting configurations such as a beveled edge can be utilized. Moreover, the instrument can be either disposable or reusable. Therefore, the above described should not be construed as limiting, but merely as exemplifications of preferred embodiments. Those skilled in the art will envision other modifications within the scope and spirit of the claims appended hereto.

What is claimed is:

1. A surgical apparatus for cutting and storing sections of body tissue comprising:
   a housing;
   an elongated outer tube extending from the housing;
   a cutting tube positioned within the outer tube and movable between a retracted position and an advanced position to cut body tissue, the cutting tube having a chamber formed therein for storing cut tissue sections;
   a handle assembly mounted to the housing in operative engagement with the cutting tube, the handle assembly movable between a first position corresponding to the retracted position of the cutting tube and a second position corresponding to the advanced position of the cutting tube; and
   a plug assembly at least partially disposed within a proximal end of the cutting tube such that a grasping end portion of the plug assembly extends proximally beyond the proximal end of the cutting tube and beyond the housing when the handle assembly is in at least the first position thereof, the plug assembly being removable from the cutting tube to access the cut tissue sections within the chamber by manual engagement with the grasping end portion.

2. The apparatus of claim 1, further comprising an anvil positioned at a distal end of the outer tube and configured for forcing each cut tissue section proximally into the chamber of the cutting tube as the cutting tube is advanced to cut the body tissue.

3. The apparatus of claim 2, wherein the cutting tube is removably mounted within the outer tube.

4. The apparatus of claim 2, wherein the outer tube has a window at a distal end to receive body tissue and wherein the anvil is positioned distally of the window in the outer tube.

5. The apparatus of claim 4, wherein the anvil is positioned at an angle to a longitudinal axis of the outer tube.

6. The apparatus of claim 1, wherein the plug assembly includes at least one ear engagable with a slot formed in the cutting tube.

7. The apparatus of claim 6, wherein the plug assembly comprises a retaining member, the at least one ear extending from the retaining member.

8. The apparatus of claim 6, wherein the plug assembly includes a plug and a retaining member for retaining the plug on the cutting tube, wherein the plug is removable only when the cutting tube is removed from the outer tube.

9. The apparatus of claim 8, wherein the retaining member has at least one ear extending into a notch in the cutting tube such that pulling on the plug cams the at least one ear further into engagement with the notch.

10. The apparatus of claim 9, wherein the retaining member is removable from the cutting tube in order to remove the plug, the retaining member being accessible only when the cutting tube is removed from the outer tube.

11. The apparatus of claim 8, wherein the handle assembly includes a trigger movable from the first position to the second position to advance the cutting tube, and further movable to a release position to enable release of the cutting tube.

12. The apparatus of claim 11, wherein the release position of the trigger is distal of the first position.

13. The apparatus of claim 12, wherein movement of the release lever to a release position moves the trigger to the release position out of blocking engagement with the plug assembly.

14. The apparatus of claim 1, further comprising a release lever engagable with the handle assembly for releasing the cutting tube.

15. The apparatus of claim 1, further comprising a rotatable knob operatively associated with the outer tube for rotating the outer tube with respect to the handle assembly.

16. The apparatus of claim 15, further comprising a locking member movable between a first position to prevent rotation of the knob and a second position to allow rotation of the knob.

17. The apparatus of claim 16, wherein the locking member is spring biased to the first position.

18. The apparatus of claim 1 wherein the plug assembly is dimensioned such that the grasping end portion of the plug assembly extends beyond the housing when the handle is in at least the first position thereof.

19. A surgical apparatus for cutting and storing tissue comprising:
   a housing including a handle assembly;
   an elongated body portion extending from the housing;
   a cutting tube slidably positioned within the elongated body portion for movement upon actuation of the handle assembly from a proximal position to a distal position to cut body tissue, the cutting tube having an open distal end;
   a rotation knob for rotating the elongated body portion about its longitudinal axis; and
   a manually engageable and manipulable locking member mounted to the housing and movable relative to the housing between a first position in engagement with the rotation knob to prevent rotation of the rotation knob and a second position disengaged from the rotation knob to permit rotation thereof.

20. The apparatus of claim 19, further comprising a tissue engaging member fixedly positioned at a distal end of the elongated body portion for forcing body tissue proximally within the cutting tube as the cutting tube is advanced to cut body tissue.

21. The apparatus of claim 18, wherein the locking member is spring biased to the first position.

22. The apparatus as claim 21, wherein the cutting tube is removably mounted in the elongated body portion to allow release thereof to access the body tissue.

23. The apparatus of claim 22, wherein the cutting tube has an opening at a proximal end and a plug assembly is removably mounted to the proximal end, the plug assembly being removable from the cutting tube only when the cutting tube is removed from the elongated body portion.

24. The apparatus of claim 23, wherein at least a portion of the tissue engaging member enters the open distal end of the cutting tube when the cutting tube is advanced to the distal position to thereby force the tissue proximally.

25. The apparatus of claim 18 wherein the locking member is movable between the first and second positions independent of movement of the rotation knob.

26. A surgical apparatus for cutting and storing tissue comprising:
   a handle assembly including a housing and a trigger mounted to the housing and being movable between at least a first position and a second position;
   an elongated body portion extending from the housing of the handle assembly;
   a cutting tube slidably positioned within the elongated body portion for movement upon actuation of the trigger from a proximal position to a distal position to cut body tissue, the cutting tube having an open distal end; and a manually engageable and manipulable release lever pivotally mounted to the housing about a mounting pin connected to the housing, the release lever engagable with the trigger and movable independent of movement of the trigger from a blocking position in engagement with the trigger to a release position in disengagement with the trigger to thereby release the trigger to allow the cutting tube to be removed from the elongated body portion.

27. A surgical apparatus of claim 26 wherein the mounting pin includes a shank mounted to the housing of the handle assembly, and the trigger includes a notch blocked by the shank when the lever is in the blocking position.

28. A surgical apparatus of claim 27, where the release lever is spring biased to the release position.

29. A surgical apparatus of claim 28, wherein movement of the release lever to the release position enables the trigger to pivot to a release position.

30. A surgical apparatus of claim 29, wherein the shank has a planar surface which aligns with the notch in the trigger when the release lever is moved to the release position.

31. A surgical apparatus for cutting and storing sections of body tissue, which comprises:
   a housing;
   an outer tube connected to the housing and extending distally therefrom, the outer tube defining an opening in a side wall thereof adjacent a distal end of the outer tube, the opening dimensioned to receive body tissue therein;
   a cutting tube disposed within the outer tube and movable therewithin from an unadvanced position to an advanced position to cut body tissue received within the opening of the outer tube, the cutting tube having a longitudinal opening defining a chamber to receive cut body tissue sections;
   a trigger mounted to the housing and in operative engagement with the cutting tube, the trigger movable to cause corresponding movement of the cutting tube from the unadvanced position to the advanced position;
   an anvil mounted to the outer tube adjacent the opening, the anvil dimensioned to force the cut body tissue sections proximally within the chamber of the cutting tube upon movent of the cutting tube to the advanced position thereof;
   a plug assembly at least partially disposed within a proximal end of the cutting tube and being releasably mounted thereto to permit access to the cut body tissue sections within the chamber, the plug assembly including a plug for enclosing the chamber of the cutting tube and a grasping portion dimensioned to be grasped by an operator to remove the plug assembly from the cutting tube; and
   a manually operable release lever mounted to the housing and engagable with the trigger, the release member movable relative to the housing to a release position to permit the trigger to move to an inoperative position wherein the trigger is in operative disengagement with the cutting tube, to thereby permit removal of the cutting tube from the outer tube.

32. The apparatus according to claim 31 including a rotatable knob rotatably mounted to the housing and in operative engagement with the outer tube, the rotatable knob rotatable to rotate the outer tube and position the opening of the outer tube at a predetermined angular orientation.

33. A surgical apparatus for cutting and storing sections of body tissue, which comprises:
   a housing;
   an outer tube connected to the housing and extending distally therefrom, the outer tube defining an opening in a side wall thereof adjacent a distal end of the outer tube, the opening dimensioned to receive body tissue therein;
   a cutting tube disposed within the outer tube and movable therewithin from an unadvanced position to an advanced position to cut body tissue received within the opening of the outer tube, the cutting tube having a longitudinal opening defining a chamber to receive cut body tissue sections;
   a trigger mounted to the housing and in operative engagement with the cutting tube, the trigger movable to cause corresponding movement of the cutting tube from the unadvanced position to the advanced position,
   an anvil mounted to the outer tube adjacent the opening, the anvil dimensioned to force the cut body tissue sections proximally within the chamber of the cutting tube upon movement of the cutting tube to the advanced position thereof;
   a plug assembly at least partially disposed within a proximal end of the cutting tube and being releasably mounted thereto to permit access to the cut body tissue sections within the chamber, the plug assembly including a plug for enclosing the chamber of the cutting tube and a grasping portion dimensioned to be grasped by an operator to remove the plug assembly from the cutting tube;
   a manually operable release lever mounted to the housing and engagable with the trigger, the release member movable to a release position to permit the trigger to move to an inoperative position wherein the trigger is in operative disengagement with the cutting tube, to thereby permit removal of the cutting tube from the outer tube;
   wherein the trigger is in direct engagement with the plug assembly to cause movement of the cutting tube and wherein movement of the release lever to the inoperative position causes release of the trigger from engagement with the plug assembly to thereby permit removal of the plug assembly and the cutting tube from the outer tube.

* * * * *